United States Patent [19]
Radtke

[11] Patent Number: 5,188,635
[45] Date of Patent: Feb. 23, 1993

[54] CATHETER FOR PERCUTANEOUS SURGERY OF BLOOD VESSELS AND ORGANS USING RADIANT ENERGY

[76] Inventor: Wolfgang Radtke, Eislebenstrasse 17, D-2800 Bremen, Fed. Rep. of Germany

[21] Appl. No.: 573,021
[22] PCT Filed: Jan. 5, 1989
[86] PCT No.: PCT/EP89/00005
   § 371 Date: Aug. 2, 1990
   § 102(e) Date: Aug. 2, 1990
[87] PCT Pub. No.: WO89/06935
   PCT Pub. Date: Aug. 10, 1989

[30] Foreign Application Priority Data
   Feb. 8, 1988 [DE] Fed. Rep. of Germany ....... 3803697

[51] Int. Cl.$^5$ ............................................. A61B 17/22
[52] U.S. Cl. ........................................... 606/14; 606/7; 606/15; 606/198
[58] Field of Search ............ 606/2, 3, 7, 13-17, 606/198; 604/104, 105, 106; 128/395-398

[56] References Cited

U.S. PATENT DOCUMENTS

| | | | |
|---|---|---|---|
| 3,557,794 | 1/1971 | Van Patten | 606/198 |
| 3,568,659 | 3/1971 | Karnegis | 604/105 X |
| 4,747,405 | 5/1988 | Leckrone | 606/15 X |
| 4,793,359 | 12/1988 | Sharrow | 606/7 X |
| 4,862,887 | 9/1989 | Weber et al. | 606/7 X |
| 4,875,897 | 10/1989 | Lee | 606/7 X |
| 4,878,492 | 11/1989 | Sinofsky et al. | 606/16 X |
| 4,961,738 | 10/1990 | Mackin | 606/15 |
| 5,034,001 | 7/1991 | Garrison et al. | 606/198 X |

FOREIGN PATENT DOCUMENTS 189329  7/1986  European Pat. Off. ............... 606/7

*Primary Examiner*—Peter A. Aschenbrenner
*Attorney, Agent, or Firm*—Alfred M. Walker

[57] ABSTRACT

A catheter for percutaneous surgery of blood vessels and organs using radiant energy, such as laser or radiofrequency radiation is provided, preferably for percutaneous valvotomy and for incision of membranous obstructions in vessels and hollow organs, especially in cardiac cavities. The catheter contains at least one light conductor, such as a waveguide, for EKG timed transmission of the energy radiation from its source to the point of emission of the radiation close to the distal end of the catheter. The EKG times and triggers the pulses of radiation when a heart valve is in the open position of a heartbeat. The catheter has a positioning mechanism so that the distal end of the catheter can anchor reversably and removably in a form fitting manner on a vessel or hollow organ part. The catheter protrudes into the lumen of the vessel or hollow organ part while leaving a throughput opening.

14 Claims, 2 Drawing Sheets

CATHETER FOR PERCUTANEOUS SURGERY OF BLOOD VESSELS AND ORGANS USING RADIANT ENERGY

This application is based upon PCT patent application number PCT/EP89/00005 filed Jan. 5, 1989, which is based upon German patent application number P 38 03 697.5-35, filed Aug. 2, 1988.

BACKGROUND OF THE INVENTION

1. Field of the Invention

The present invention refers to a catheter device useful for percutaneous surgery of blood vessels and organs. The catheter uses radiant energy, such as laser high frequency or radiofrequency radiation, preferably for percutaneous cardiac surgery, such as valvotomy. It is also used for incision of membranous obstructions in blood vessels and hollow organs, especially in cardiac cavities. The catheter utilizes at least one light conductor, such as a waveguide, to transmit the energy radiation from its source to the point of emission of the radiation at a location close to the distal catheter tip. In a preferred embodiment by means of EKG timed and triggered pulsed radiant energy, the catheter is used to perform surgical procedures only when the cardiac valve is open.

2. Description of the Prior Art

Laser catheters for cardiac vessel surgery, such as is disclosed in U.S. Pat. No. 4,207,874, are being used to recanalize the interior of blocked blood vessels. Such catheters are discussed in Choy "Vascular recanalization with the laser catheter", IEEE Journal of Quantum Electronics, No. 12, 1984, pp. 1420-1426. In this prior device the catheter is percutaneously inserted into the blood vessel and its distal tip is advanced through the vessel up to the point of obstruction of the blood vessel caused by a thrombus or by an atherosclerotic plaque upon the walls of the blood vessel. During subsequent removal of the blockage by laser radiation, perforation of the vessel wall can occur, if the point of laser emission, typically located at the distal end of catheter tip, is not properly aimed at the obstruction of plaque or if the penetration depth of the laser light into the blood vessel exceeds the depth of the obstruction of plaque within the blood vessel.

A device to align the point of emission in a laser catheter was proposed for a catheter with an inflatable balloon at its distal end in U.S. Pat. No. 4,627,436 and in Nordstrom et al., "Laser angioplasty: controlled delivery of Argon laser energy" Radiology 167, 1988, pp. 463-465) centering or otherwise directing the laser radiation emitted from the fiber. The balloon in this device, however, completely obstructs the lumen of the blood vessel. In addition, the balloon can only be positioned in relatively narrow blood vessels and not in hollow organs, especially not in the cardiac cavity or at cardiac valves.

Furthermore, a laser catheter was employed in animal experiments to incise the septal cardiac muscle as noted in Isner et al. "The current status of lasers in the treatment of cardiovascular disease", IEEE Journal of Quantum Electronics, No. 12, 1984, pp. 1406-1418). The catheter in Isner was inserted percutaneously and advanced to the heart of dogs under echocardiographic guidance, where upon direct contact between the point of light emission and cardiac muscle the incision was possible, but selective positioning of the point of light emission at a predetermined location was not possible. Intraoperatively, a septal incision in a human heart was performed under direct vision.

From in-vitro experiments with postmortem specimen and from animal experiments, it is also known that laser catheters can be used to ablate membranous septum in the heart and to remove obstructions in large vessels, as noted in Riemenschneider et al., "Laser irradiation of congenital heart disease: Potential for palliation and correction of intracardiac and intravascular defects", Am Heart J 106, 1983, pp. 1389-1393). In the in-vitro experiments described in Riemenschneider the catheters were directly inserted into the specimen from the outside, while a relatively nonselective perforation of the cardiac septum could be performed in the animal experiments using a percutaneously inserted catheter.

SUMMARY OF THE INVENTION

The purpose of this invention is to develop a catheter device for percutaneous surgery of blood vessels and organs using radiant energy, such as laser or high frequency radiation, which can be positioned exactly at the location of the point of operation, within the blood vessel or organ, without interrupting blood flow and/or organ activity.

The inventive solution of the above mentioned task is provided in a catheter device, for percutaneous surgery of blood vessels and organs, which device uses radiant energy such as laser, high frequency or radiofrequency radiation. The device is used preferably for percutaneous valvotomy surgery and for incision of membranous obstructions in blood vessels and hollow organs, especially in cardiac cavities. The device contains at least one light conductor, such as a wave guide for transmission of the energy radiation from its source to the point of emission of the radiation nearest to the distal end of the catheter end. The catheter device has a positioning mechanism by which the distal end of the catheter can anchor itself in a removable, reversably form fitting manner upon the inner surface of a blood vessel or a hollow organ, while at the same time leaving a throughput opening within the blood vessel or hollow organ. Further preferred embodiments and variations are noted in the following description of the preferred embodiment, as noted in conjunction with the following drawings.

The core of the invention is to equip the catheter device with a positioning mechanism which can preferably be handled by the surgeon from the proximal catheter end of the catheter device. The catheter device allows exact positioning of the device without the problems of blood vessel obstruction, and reversable anchoring at the narrowing of the blood vessel or hollow organ, caused by vascular or organ parts, or other protrusions, in order to provide the necessary surgical conditions to aim accurately the laser or other energy radiation at the target within the blood vessel or hollow organ subject to incision.

According to a preferred embodiment of the invention, the positioning mechanism can be anchored on the free edge of the cardiac valve during uninterrupted valvular activity, so that the catheter device can be employed to open stenotic heart valves or membranous stenoses. Hereby, the laser energy radiation is EKG timed and triggered, that is, it is emitted and preferably launched into the light conductor, such as a waveguide, while the cardiac valve is open. To ensure exact aiming of the laser energy radiation at the intended point of incision within the blood vessel or hollow organ, such as the heart, the laser energy radiation light conductor, such as a waveguide, is at least located in the region of the point of emission of the radiation. The light conductor, such as a waveguide, is combined with a positioning element of the positioning mechanism so that the point of emission of the laser energy radiation is fixed directly at the intended target site within the blood vessel or hollow organ, such as the heart.

According to one preferred embodiment of the invention the positioning mechanism of the device includes at least one pair of wires, the wires of which extend along the axis of the catheter. At the distal catheter end the wires can be spread out from a ground position closely adherent to the catheter surface to form two elastically flexible convex wire arches radially extending over the catheter surface and axially displaced against each other so that an indentation is formed at the intersection of the wire arches, to anchor the catheter form fitting to the edge of a heart valve. One or more, preferably two or three, of the wire pairs, which are made of metal or plastic, are proposed. Upon spreading, the wire pairs position themselves in the angles of the fishmouth or triangular shaped cardiac valve ostium of the heart.

In another preferred embodiment of the invention, the ends of the wire arches of each wire pair are axially displaced against each other. The ends of the wire arches are firmly attached to two preferably coaxially arranged catheter components, which components can be moved against each other in axial direction. By axially shifting the catheter components against each other at the proximal end of the catheter, the wire pairs are straightened to flatly adhere to the catheter surface during insertion and removal of the catheter. When in use, the wire pairs are spread so that the indentation forming at the intersection between the arches anchors the catheter on the edge of a cardiac valve of the heart. This anchoring of the catheter secures the distal catheter end against unwanted displacement.

According a modified embodiment of the invention, the wires are axially movable relative to the catheter and are firmly attached to the catheter only at the distal ends of the arches of the wires.

At least one of both wires, preferably the wire forming the proximal arch of each wire pair, is combined with a light conductor, such as a waveguide, for transmission of laser radiation. The wire and the light conductor, such as a waveguide, are arranged in parallel and are preferably enclosed in a common coating. By placing the point of emission of the laser light on the wire arch formed during spreading of the wires, a defined spatial alignment, e.g. between the point of light emission and the edge of a valve fixed within the indentation, can be achieved to surgically incise a stenotic cardiac valve. The direction of emitted laser radiation can be monitored continuously during the surgical operation because the wire with the point of light emission is visible by fluoroscopy and echocardiography, and the angle of laser radiation relative to the wire is known. In order to perform multiple surgical incisions simultaneously or sequentially without moving the catheter, it is useful to attach light conductors, such as waveguides, to more than one or all of the wires.

In a further preferred embodiment of the invention the point of light emission is located and placed in the region of the indentation formed upon spreading of the wires, preferably proximal to the intersection of the wire arches The point of laser light emission, thereby, is in direct contact with the target site on the vascular or organ part that is anchored in the indentation of the wires of the catheter device.

In another preferred embodiment of the invention the degree of the spreading of the wire arches is variable. The spreading of the wires is preferably adjustable using a spring, so that the wire arches remain in contact with the vessel or organ part to be incised. By means of a self-acting increase in the degree of spreading of the wire arches during incision, the location of the point of laser light emission is advanced until the end of the incision, so that controlled cuts of variable depth can be performed.

DESCRIPTION OF THE PREFERRED EMBODIMENT

Figure 1:
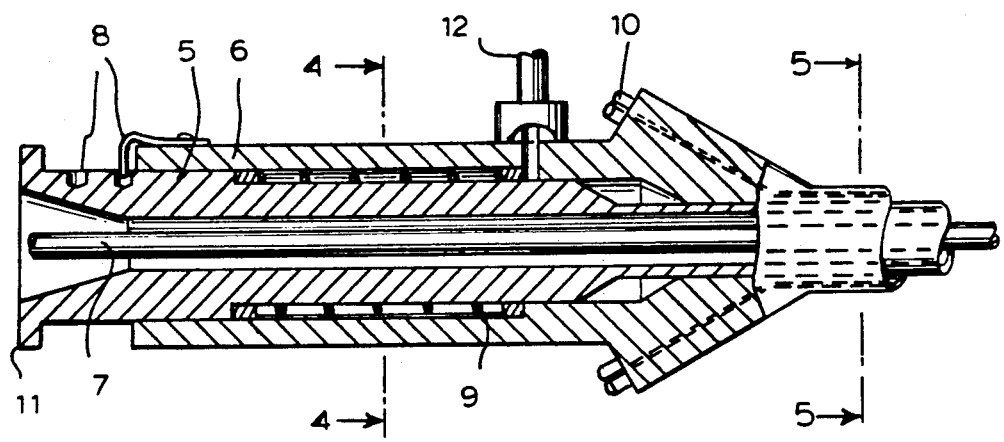
FIG. 1 is a side view of the proximal catheter end of the device partly in section.
Figure 2:
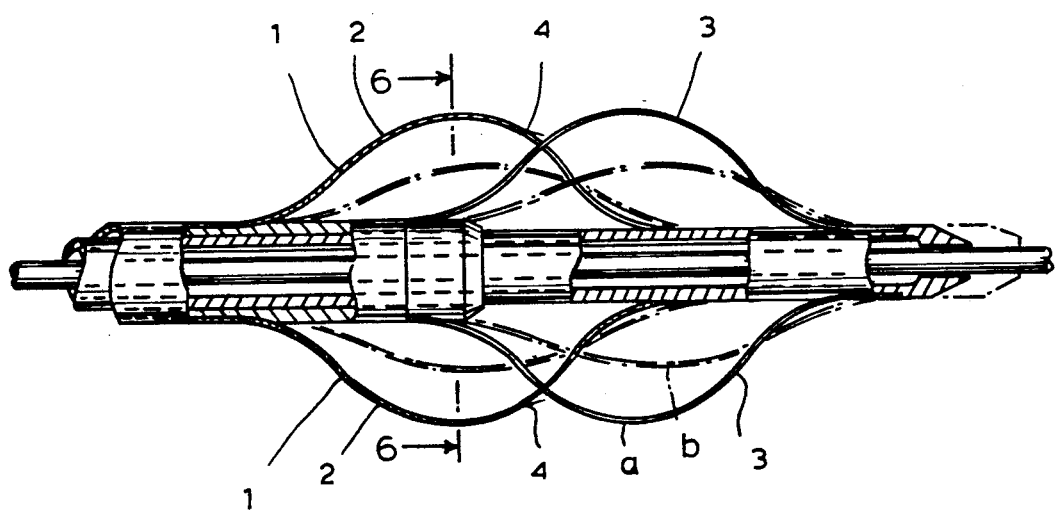
FIG. 2 is a side view of the distal catheter end partly in section showing wire pairs completely spread and partly spread.
Figure 3:
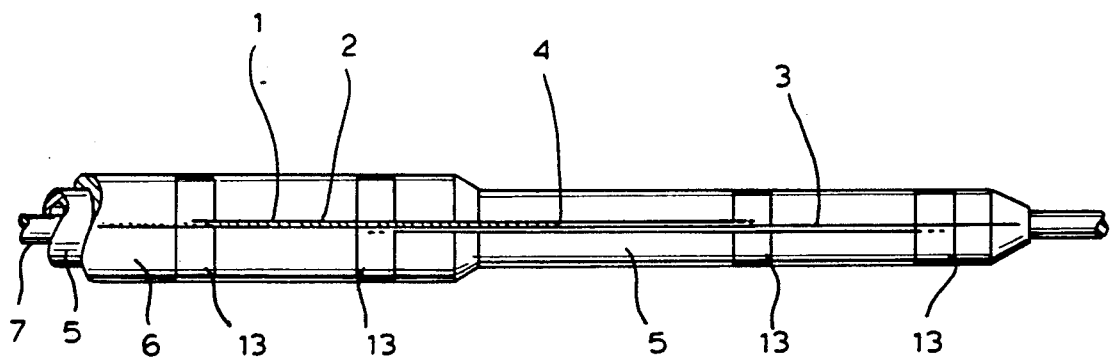
FIG. 3 is an end view of the distal catheter end with flat wire pairs.
Figure 4:
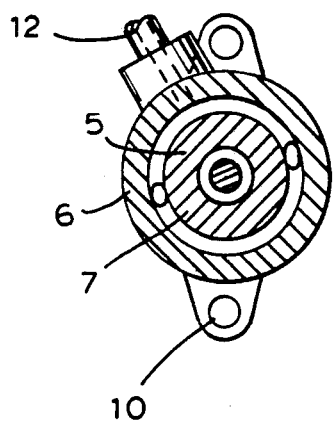
FIG. 4 is a cross sectional view of the catheter along line A—A of FIG. 1.
Figure 5:
FIG. 5 is a cross sectional view of the catheter along line B—B of FIG. 1.
Figure 6:
FIG. 6 is a cross sectional view of the catheter along line C—C of FIG. 2.

The catheter includes two coaxially arranged catheter components 5, 6 that are axially movable against each other. The inner catheter component 5 is equipped with a Luer-Lok connector 11 at the proximal end and has an axially continuous lumen 20 to accommodate a guide wire 7 along which the catheter is inserted. A click-stop device at the proximal end of the outer catheter component 6 arrests both catheter components 5, 6 against each other when hooking into grooves 22 and 23 of the catheter components. Grooves 22, 23 are located on the inner catheter component 5 in a manner that the click-stop device 8 is activated in the two positions that correspond with the flat (c) and the maximally spread position (a) of the wire pairs as shown in FIGS. 2 and 3. After release of the click-stop device 8 out of the groove 22, a spring 9 located between inner catheter component 5 and outer catheter component 6 shifts the catheter components 5 and 6 axially against each other until the wire pairs 2, 3 with their indentation 25, anchor on the blood vessel obstruction or organ part to be incised. A tube connector 12 serves to flush the space between inner catheter component 5 and outer catheter component 6. An axial guide (not shown) prevents rotation of catheter components 5 and 6 against each other. Each of the coated light conductors, such as waveguides, 14 extend from their entry on both sides of the proximal catheter end to the wire pairs 2, 3 at the distal catheter end. The light conductors, such as waveguides, are coupled separately or combined via a connector to the laser source not shown.

Figure 7:
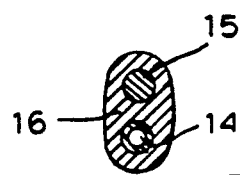
FIG. 7 is a cross sectional view of the wire combined with the waveguide.

The metal or plastic wires 2, 3 of both partly (b) or fully (a) spread wire pairs of the distal catheter end shown in FIG. 2 cross each other, the wires 2, 3 forming an indentation 25 which serves to position and anchor the catheter in place. The proximal ends of wires 2, 3 are axially displaced against each other and are attached to the outer catheter component 6. The distal ends of wires 2, 3, which are also being axially displaced against each other, are attached to the inner catheter component 5. Four light conductors such as waveguides 14, extend from the proximal catheter end in the wall of the outer catheter component 6 and exit the surface of the outer catheter component 6, together with the wires 2, 3 to run parallel to wires 2, 3 up to the location of the point of light emission 4. At the location of the point of light emission 4 each light conductor, such as waveguide, 14 and a wire 2 or 3, respectively, are enclosed in a common coating 16 as shown in FIG. 7. The point of light emission 4 is constructed in a way that the laser radiation is emitted tangentially to the wire arch as indicated by the small arrows as shown in FIG. 2. The points of attachment of wires 2, 3 with the inner catheter component 5 and outer catheter component 6, respectively, are reinforced with a thin metal ring 13. In the ground position of both catheter components 5 and 6 depicted in FIG. 3 the wire pairs 2, 3 are straight and flatly adherent to the catheter surface. The click-stop device 8, which is located at the proximal catheter end, hooks into groove 22 in this position.

After the diagnosis of a membranous or valvular stenosis is made during cardiac catheterization, a guide wire 7 is positioned across the stenotic valve so that the described valvotomy catheter can be inserted with straight wires 2, 3 flatly adherent to the catheter surface. The catheter is then positioned in the valvular ostium so that the wire pairs position themselves in the angles of the fishmouth or triangular shaped valve ostium upon spreading, whereby the middle of the distal wire arch 3 comes to lie distal to the cardiac valve. The middle of the proximal wire arch 2 comes to lie proximal to the cardiac valve. After disengaging the click-stop device 8 out of groove 22, the inner catheter component 5 is shifted axially against the outer catheter component 6 by the spring 9 spreading the wire pairs until the edge of the stenotic heart valve anchors in the indentation 25, which forms at the intersection of the wires 2, 3 upon spreading of the wire pairs. Positioning and aiming of the point of laser light emission 4 is monitored fluoroscopically and by 2D-echocardiography. After positioning of the distal catheter end in the region of the commissures to be separated, the points of laser light emission 4 lie in direct contact with the target of incision, so that after coupling to the laser source, e.g. an excimer, holmium or erbium laser, the incision of the free edge of the stenotic heart valve can commence.

The laser radiation is emitted and pushed against the targeted site only in the exact time interval when the cardiac valve is open, when the EKG so notes the open position of the cardiac valve and permits the laser light to emit an incisive surgical pulse. By means of EKG timed and triggered pulsed laser radiation, the valvotomy is performed while the cardiac valve is open. After the initial surgical incision the point of laser light emission 4 is adjusted by means of self-acting spreading of the wires up to the location of the end of the incision so that controlled incisions of variable depth can be performed. The depth of incision is determined on the basis of prior measurements of the cardiac valve annulus.

I claim:

1. A catheter for percutaneous surgery of blood vessels and organs using radiant energy such as laser or radio frequency radiation, preferably for percutaneous valvotomy and for incision of membranous obstructions in blood vessels and hollow organs, especially in cardiac cavities comprising:
    at least one energy conductor for transmission of said energy radiation from its source to the point of emission of said radiation close to the distal catheter end,
    said catheter including a positioning mechanism by means of which said distal catheter end can anchor reversibly, removably and form fitting on one of said vessels or organ parts, said distal catheter end protruding into the lumen of said vessel or hollow organ while leaving a throughput opening in said vessel or hollow organ;
    said positioning mechanism including:
    at least one pair of wires, the wires of which extend substantially parallel to the axis of said catheter and
    said wires being spreadable at the distal end of said catheter from a ground position flat and closely adherent to the surface of said catheter,
    said wires forming two convex elastically flexible wire arches radially extending over said catheter surface,
    said wires being axially displaced against each other and said wires intersecting each other,
    said wires forming an indentation at the intersection of said wire arches for form fitting anchoring of said catheter on said vessel or organ part.

2. The catheter according to claim 1 wherein by means of said positioning mechanism the point of emission of said energy radiation can be aimed at a preferred surgical target located in said vessel or organ part.

3. The catheter according to claim 1 wherein said light conductor for said energy radiation is located in the region of the point of emission of said energy radiation and said light conductor is combined with a positioning element of said positioning mechanism that anchors on said vessel or organ part.

4. The catheter according to claim 1 comprising
    at least two pairs of wires, preferably arranged at equal angles to each other.

5. The catheter according to claim 1 wherein said wires of each pair of wires are axially displaced against each other at their arch ends and
    said wires are firmly attached to two components of said catheter
    said components being arranged coaxially and
    said components being axially movable against each other.

6. The catheter according to claim 1 wherein said wires are axially movable relative to said catheter and
    said wires at their distal ends of said arches are firmly attached to said catheter.

7. The catheter according to claim 1 wherein at least one of both of said wires, namely said wire forming the proximal arch of each pair of wires carries a light conductor for laser radiation, said wire extending substantially parallel and enclosed in a common coating and
    wherein the point of emission of said radiation is located in the region of said wire arch that is formed during spreading of said wires.

8. The catheter according to claim 7 wherein each wire of each said pair of wires carries a light conductor.

9. The catheter according to claim 7 wherein the point of said laser light emission is located close to said indentation formed when the said wires are spread, and
    said point of laser light emission is proximal to the intersection of said wire arches.

10. The catheter according to claim 1, wherein the degree of spreading of said wires is variable.

11. The catheter according to claim 1 wherein said degree of spreading of said wires is adjustable, by means of a spring, said wire arches remaining in contact with said vessel or organ part to be treated by said catheter.

12. The catheter according to claim 1 wherein said positioning mechanism is anchorable on the valve of a beating heart and said energy radiation is launched into said light conductor by EKG trigger, while said cardiac valve is open.

13. The catheter according to claim 1 wherein said positioning mechanism is handled from the proximal end of said catheter.

14. The catheter according to claim 1 wherein the light conductor is a waveguide.

* * * * *